United States Patent [19]

Polz

[11] Patent Number: 5,632,619

[45] Date of Patent: May 27, 1997

[54] JAW ARTICULATOR AND FACE BOW WITH BITE-FORK COLUMN

[76] Inventor: Michael H. Polz, Waldmüllerstrasse 12, D-8520 Erlangen, Germany

[21] Appl. No.: 705,074

[22] Filed: Aug. 27, 1996

Related U.S. Application Data

[60] Continuation of Ser. No. 280,200, Jul. 25, 1994, abandoned, which is a division of Ser. No. 972,499, Feb. 5, 1993, Pat. No. 5,385,470.

[30] Foreign Application Priority Data

Aug. 8, 1990 [DE] Germany ............... 40 25 121.7
Aug. 8, 1991 [WO] WIPO ............ PCT/EP91/01498

[51] Int. Cl.$^6$ .................. A61C 11/00; A61C 19/04
[52] U.S. Cl. ................... 433/57; 433/68; 433/73
[58] Field of Search .................. 433/54, 57, 68, 433/70, 73

[56] References Cited

U.S. PATENT DOCUMENTS

| | | | |
|---|---|---|---|
| 1,786,915 | 12/1930 | McLean | 433/73 |
| 3,218,716 | 11/1965 | Stuart | 433/73 |
| 3,528,176 | 9/1970 | Lee et al. | 433/73 |
| 3,866,323 | 2/1975 | Granger | 433/73 |
| 4,639,220 | 1/1987 | Nara et al. | 433/73 X |
| 4,695,252 | 9/1987 | Edwardson | 433/73 |
| 4,836,779 | 6/1989 | Beu | 433/73 |
| 4,892,480 | 1/1990 | Levandoski | 433/73 |
| 5,009,594 | 4/1991 | West | 433/73 |
| 5,090,901 | 2/1992 | Levandoski | 433/73 X |

*Primary Examiner*—Nicholas D. Lucchesi
*Attorney, Agent, or Firm*—Frank H. Foster; Kremblas, Foster, Millard & Pollick

[57] ABSTRACT

A face bow for receiving and transferring a model jaw to a jaw articulator in the correct spacial orientation relative to a patient's skull and jaw hinge axis. The face bow has a curved transfer member for surrounding a patient's face and a guide column releasably secured to the transfer member for carrying an adjustable bite fork. The transfer member has an elongate, centering groove and the guide column has an adjusting projection which is perpendicular to the guide column for engagement in the centering groove.

15 Claims, 7 Drawing Sheets

JAW ARTICULATOR AND FACE BOW WITH BITE-FORK COLUMN

This is a continuation of application No. 08/280,200, filed Jul. 25, 1994, now abandoned, which was a division of application No. 07/972,499, filed Feb. 5, 1993, now U.S. Pat. No. 5,385,470, issued Jan. 31, 1995.

FIELD OF THE INVENTION

The invention relates to a articulator for simulating jaw movements, comprising an upper and a lower part for carrying an upper-jaw and/or a lower-jaw model and connected by joints permitting one or more swivelling and linear motions. The invention also relates to a face bow comprising a curved transfer member surrounding the face and for transferring and fitting a model jaw in the correct spatial orientation relative to the skull in an aforementioned jaw articulator; the end regions of the transfer member are equipped with scanners for locating the pivot axis of the hinge of the jaw, in order to attach it to the transfer member at the reference points of the hinge axis.

BACKGROUND ART

Devices of this kind are known in dental technology (compare W. Hoffmann-Axthelm "Lexikon der Zahnmedizin", Quintessens-Verlags GmbH Berlin, 1983; "Einführung in die Zahnersatzkunde", Verlag Urban und Schwarzenberg, 1975).

The jaw articulator is for simulating movements of the hinge of the jaw when dental and jaw models are inserted, and the articulator can practically completely simulate the motion of the jaws relative to one another outside the mouth. The main problem in jaw articulation is to provide an average simulation of substantially all movements of the human lower jaw relative to the upper jaw. Articulators known for this purpose have very many adjustment facilities. The adjustment is made in accordance with a pantographic (three-dimensional) recording of the individual movements of the patient's lower jaw made by the dentist. The recording is lengthy and expensive, taking about 2 to 3 hours for obtaining the information from the patient. The subsequent programming of the articulator in accordance with the pantograph takes about 3 to 5 hours.

In other known articulators, the slope of the joint path is adjustable in the sagittal direction. The motion of the condyle can also be limited, i.e. adjusted, in the transverse direction (Bennett angle). The parts of the joints in these simulators, known as Arcom articulators, are designed in accordance with anatomical conditions, i.e. the condyles are disposed on the lower part of the articulator and the condyle casing or joint box with the device for adjusting the Bennett angle are disposed on the upper part of the articulator. However, these known articulators enable the respective ball or condyle to move laterally only; in which case the straight track of the second joint box or condyle moves in the median direction. Furthermore the balls are tightly encapsulated in their boxes, and consequently do not have degrees of freedom for components of motion in other directions.

SUMMARY OF THE INVENTION

Accordingly the invention is based on the problem of constructing an articulator having sufficient reserves for motion of the jaw, in order to model a dental prosthesis which is comfortable for the patient to wear and is physiologically compatible. To this end, as proposed according to the invention in the case of an articulator having the initially-dimensioned features, in the joint the lower part is guided relative to the upper part in one or more directions comprising components of motion in the cranial and/or dorsal direction and corresponding to surtrusion and/or retrusion.

This guidance of the lower part of the articulator relative to the upper part in the joint permits average Bennett motions backwards or retrusively and/or upwards or surtrusively when modelling dental prostheses. This is a method of eliminating errors in simulating the occlusion of the upper or lower jaw; such errors would otherwise necessitate careful regrinding by the dentist and might possibly damage or destroy the entire masticatory system.

DETAILED DESCRIPTION OF PRINCIPLES OF THE INVENTION

In an embodiment of this inventive idea, the joint is formed with one or more linear guides which deviate surtrusively and/or retrusively from the direction of a common hinge-like axis connecting the joints. Angles of about 13°–17°, more particularly 15°, have been found advantageous in practice, as regards the deviation of the surtrusion and/or retrusion components of motion relative to the hinge axis. Advantageously to this end, the angle between the hinge axis and the linear guide for obtaining the aforementioned retrusion and/or surtrusion is acute and preferably about 30°.

The advantage of guiding the Bennett motions (laterotrusion) in the cranial (surtrusion) direction also according to the invention, more particularly at an angle of 15° to the hinge axis, is that the occlusion in the side-tooth region can be designed so that the freedom of motion of the lower jaw is additionally ensured in this direction. If the Bennett motion is guided not only laterally or cranially but also and particularly at 15° to the rear (retrusion) the advantage is that the motion of the lower jaw is lateral, cranial and retral instead of lateral and cranial only. This motion facility gives retral freedom in occlusion.

In the case of articulators comprising joint parts constructed under anatomical conditions with a joint box for receiving a ball of a joint, the construction and manufacture are simplified or reduced in expense if, according to another feature of the invention, one or more sliding surfaces are formed in the joint box for components of motion of the ball in the cranial and/or dorsal direction or for surtrusion and/or retrusion. The sliding surfaces thus form the guides or tracks for the ball to give it the desired freedom of motion according to the invention. In principle these sliding surfaces or tracks can be curved or bent, but it is particularly advantageous for them to be linear or straight, at least in parts.

According to another feature of the invention, account is taken of research results, according to which the joint box has internal or concave curvature, the average radius of the curvature being about three-quarters of an inch. The motion of the lower jaw thus differs from conventional average-value articulators in that the sagittal condyle track has a three-quarter inch radius.

In order to adapt the jaw hinge articulation even better to individual peculiarities of the patient's teeth or dentures, according to another feature of the invention a guide duct is provided and extends through the joint box and opens into its interior and contains an adjusting means which is guided in reciprocation so that it can engage the ball or condyle and adjust it. In this manner, the balls or condyles can deliberately be brought into a latero-protrusive or protrusive position, so as selectively to balance an existing occlusion or to restore it.

According to another feature of the invention, based on articulators with Bennett bevels on the joint for displacing the condyle, the Bennett bevel is disposed at a fixed angle of 10° to the hinge axis of the joints or to the median plane. This results in adaptation to the per se known Bennett angle of 6°–7.5°. With regard to Bennett bevels, they are advantageously made adjustable between 0 and 3 millimeters to the median plane, in accordance with an existing scale with 0.5 millimeter divisions. This is a means of individually adjusting the direct median displacement (=immediate sideshift) of the condyle.

In an alternative embodiment of an articulator having the initially-mentioned features, the upper and/or lower jaw each extend at an angle of 10° to the horizontal plane. Advantageously the slope is upwards in the dorsal direction. In other words, the two parts of the articulator for the upper and lower jaw are not parallel to the horizontal plane but, measured relative to the occlusion plane, slope upwards by 10°. This has important advantages. Three-dimensional orientation of the upper jaw in the cranial direction is made easier by raising the frame in the posterior region. The articulator frame parts are thus brought near the occlusion plane. The expansion of the plaster of Paris used in fitting the dental prosthesis is compensated in more balanced manner. As a result of the aforementioned 10° slope of the articulation frame, the assembly plate of the articulator is almost parallel to the base of the model, so as to counteract irregularities caused by the assembly material (expansion of the plaster). One advantage in manufacture, during lining, is that when the model is taken out, the occlusion planes lie parallel to the horizontal plane. A model taken out and standing horizontally on a table can be lined by using a metal into which the lining material is poured. Without the 10° inclination according to the invention, the occlusion plane would be simulated at an angle. Finally, owing to the angular adjustment of the lower and upper articulation frame (the lower and upper part), the application of force can also be concentrated on the occlusion plane; as a result of the adjustment via the aforementioned 10° inclination to the occlusion plane, the torque applied in closing the jaw is converted exclusively into a component of force directed at right angles to the occlusion plane. This avoids splitting into other, ineffective components of force parallel to the occlusion plane. This method of application of force ensures reliable and balanced occlusion.

When handling articulators, it is desirable to be able to lock the upper part and lower part at the zero point of occlusion. To this end, in the case of an articulator having the initially-mentioned features, where the parts of the joint also permit transverse or lateral components of motion of the bottom part transversely to the median or sagittal plane and/or in the direction of the hinge axis of the joints, the invention proposes a first and a second locking element which are disposed on the upper and the lower part and can be releasably brought into engagement with one another so as to eliminate lateral components of motion of the upper and lower part relative to one another. The central static position of occlusion (zero point of occlusion) is locked in this manner. Of course, in order to simulate the Bennett motion in accordance with the first-mentioned alternative, the centric locking must be released, by disengaging the first locking element from the second locking element.

In one construction corresponding to this inventive idea, one locking element is in the form of a notch or gap immovably attached to the upper and/or the lower part, whereas the other locking element is an insertion or engagement means pivotable in the first locking element and adapted to be secured and manipulated transversely or at an angle to the lateral direction; the last-mentioned means is hinged to the lower part or the upper part. According to another constructional feature, the gap is formed at the rear on the lower part by two hooks, which project side by side and are open at the top, and the engagement means is hinged to the upper part at the rear; on both sides it has lateral projections so that it can fall into the aforementioned open hooks. The advantage is that the articulator can be used either in one piece or divided, both in the open and in the closed, centrically locked state.

In order to adjust the articulator to individual patients (e.g. the Bennett angle or the intercondylar distance), the measurements must be individually recorded on the patient. In the case of the sagittal condylar inclination and the Bennett angle for example, this can be done by means of face bows (extra-oral recording). For the purpose of intra-oral determination of the sagittal condylar path inclination, the patient in the protruded (forwardly moved) position is requested to bite on a bite fork in a wax recording device. In this case the condyles are in a position which is typical of the respective individual inclination of the joint track. If the wax recording device is inserted between the rows of teeth in dental jaw models secured in an articulator at an adjustable inclination of the condyle track, and if the model jaw is inserted exactly into the wax recording device, the movements of the articulator will substantially correspond to the individual movements of the patient's jaw hinge. The articulator joint can therefore be adjusted in this manner to the individual inclination of the patient's joint track.

To simplify the manipulation of the hinge axis reference points for a patient and to locate them in accordance with his individual skull characteristics without inconveniencing the patient, in another alternative version of the invention, as proposed in the case of a face bow having the initially-mentioned features, the scanners are movable and lockable in the direction of the hinge axis.

In order symmetrically to position the transfer member of the face bow relative to the median or sagittal plane of the human jaw, according to another feature of the last-mentioned alternative, the scanners carry code markings disposed symmetrically on the respective carrier relative to the jaw median plane or a central plane transversely to the hinge axis; the carriers can move in the direction of the hinge axis past reference marks disposed in a stationary position on the transfer member. In an embodiment of this idea, the scanners are bolts or pins which extend through the ends of the transfer member so as to be capable of reciprocation in the direction of the hinge axis, and comprise colored recesses and/or raised portions in the form of rotating rings which constitute the symmetrical code marks.

Optionally according to the invention the face bow having the initially-mentioned features is provided with a supporting projection which is positioned in a central portion of the transfer member and is adapted to abut the glabella (the hairless region between the eyebrows). Particularly advantageously the projection is movable, i.e. in the direction towards the glabella and/or at an angle or at right angles to the plane spanned by the transfer member, and is lockable in the position corresponding to the patient. The locking means can be one or more milled-head screws. This avoids the previously known adjustment of the transfer member to a non-exact average value relative to the glabella.

If the glabella support and the previously-explained hinge axis scanners are secured in three dimensions, e.g. by milled-head screws, in accordance with the patient's individual characteristics, the problem of transport arises after the bite fork has been taken out. The bite fork and its guiding or supporting column must be delivered to the laboratory and mounted on the articulator with three-dimensional adjustment corresponding substantially to the geometrical characteristics of the individual patient's skull. To this end it is known to remove the supporting-pin plate from the lower-jaw part of the articulator and as a substitute to secure the guiding and supporting column with the bite fork.

Faulty deviations of up to 8 millimeters can occur in the process. This is due mainly to alignment of the bite fork at an incorrect angle to the median plane of the jaw, e.g. if the guiding or supporting column and the bite fork secured thereto are not inserted and/or mounted in the articulator lower-jaw part in the correct rotary position relative to the skull.

Accordingly the invention is based on the problem of providing a face bow which is easy to manipulate and can reliably transfer the angular position of the bite fork relative to the median plane to the articulator exactly in accordance with the characteristics of the individual skull. To this end according to the invention, in the case of a face bow comprising a guide column releasably secured to the transfer member in order to carry an adjustable bite fork, according to the invention, the transfer member has an elongate centring recess on its upper or lower side and the guide column has an adjusting projection for positive engagement in the centring recess.

When the stationary centring recess on the transfer member engages the stationary adjusting projection on the guide column, the guide column is practically prevented from rotation, together with the bite fork secured thereon in the correct three-dimensional orientation relative to the skull. If the bite fork is not moved relative to the guide column, the guide column, via its adjusting projection, can be brought into a position in a suitable centring recess on the articulator, the position corresponding substantially to the three-dimensional conditions recorded on the individual patient's skull and fixed by means of the bite fork and/or the previously-explained hinge axis feelers.

Advantageously the adjusting projection is in the form of a spike projecting vertically from the guide column and/or the centring recess is a V-section groove. As a result of this cross-sectional shape, the spike is guided in the central longitudinal plane of the groove up to its base or peak, where it is substantially non-rotatably secured.

Exact adjustment relative to the patient's skull is facilitated if the centring recess extends approximately at right angles to the frontal plane of the jaw and/or the jaw hinge axis. The same applies if the centring recess extends approximately in the direction of the median plane of the jaw and/or lies in the central transverse plane of the transfer member.

In order to mount the aforementioned guide column, comprising a bite fork bearing an individual wax record of the patient, in the articulator in a rotated position corresponding to the values measured by means of the face bow, according to the invention the articulator is provided with an adapter comprising a centring recess for positively receiving the aforementioned adjusting projection of the guide column. This appreciably increases the reliability and accuracy in manipulating the articulator.

According to another feature, the articulator adapter according to the invention is formed with a bore for inserting and securing the guide column of the bite fork (e.g. by milled-head screws). The centring recess extends radially or at right angles to the bore. When therefore the guide column is inserted, its adjusting projection can serve as an abutment limiting the depth of insertion.

In order to use the adapter according to the invention also in known commercially-obtainable articulators, according to another feature the adapter is in the form of a part which can be releasably secured to the upper or lower part of the articulator. The result, particularly when the adapter is fitted to the top part of the articulator, is a closed top unit corresponding to the model taken from the patient by means of the face bow and the bite fork. The aligned hinged-axis feelers or indicators on the face bow, which have located the actual hinge axis of the patient's jaw, reproduce the upper jaw and skull unit of the individual patient in identical manner in the top part of the articulator. By this means, the upper jaw on the articulator can be adjusted to fit the skull.

BRIEF DESCRIPTION OF THE DRAWINGS

Other details, features and advantages of the invention will be clear from the following description of a preferred embodiment of the invention and from the drawings, in which.

DETAILED DESCRIPTION OF PREFERRED EMBODIMENT

Figure 1:
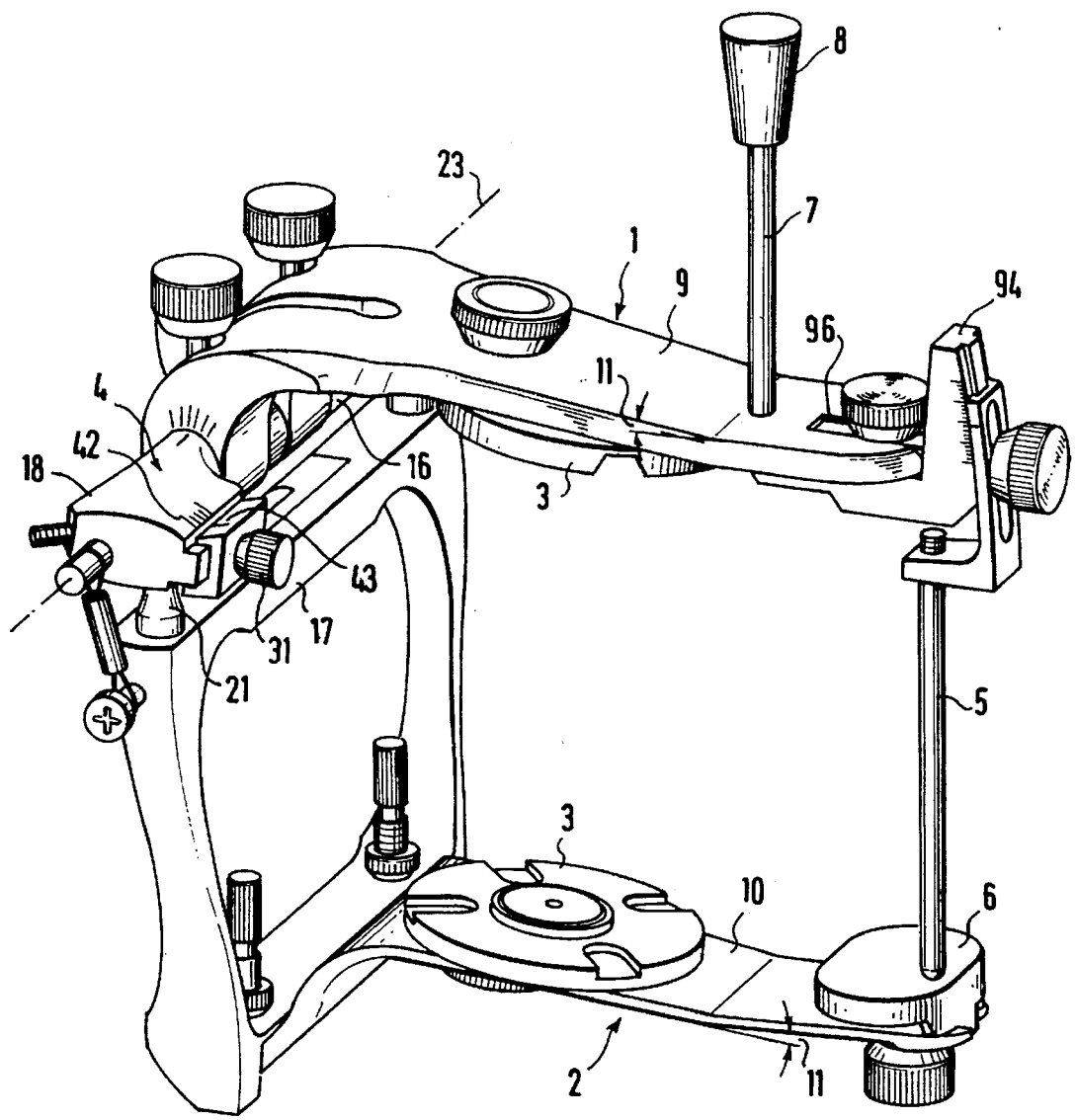
FIG. 1 is a perspective view of the articulator.
Figure 2:
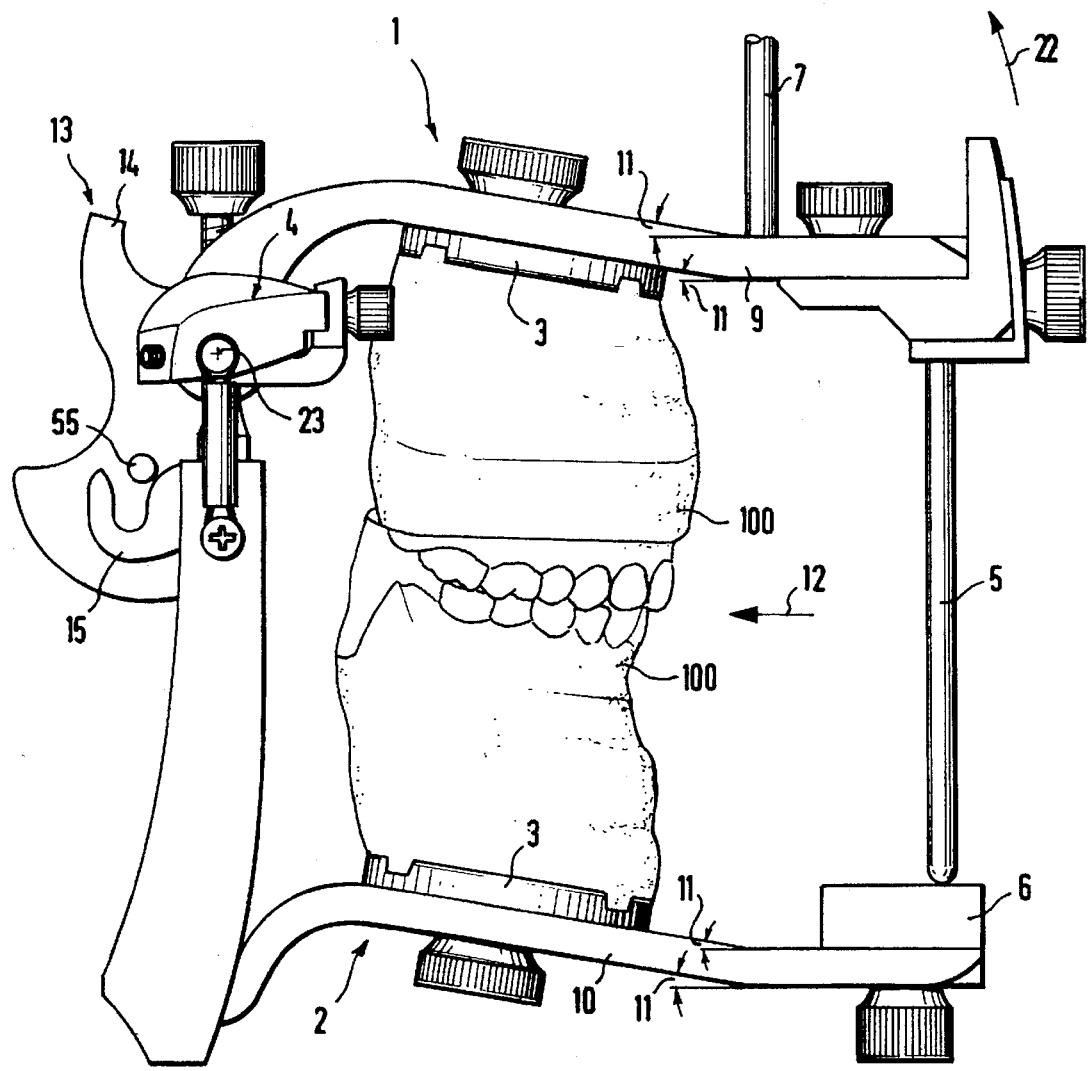
FIG. 2 is a side view of the articulator.
Figure 3:
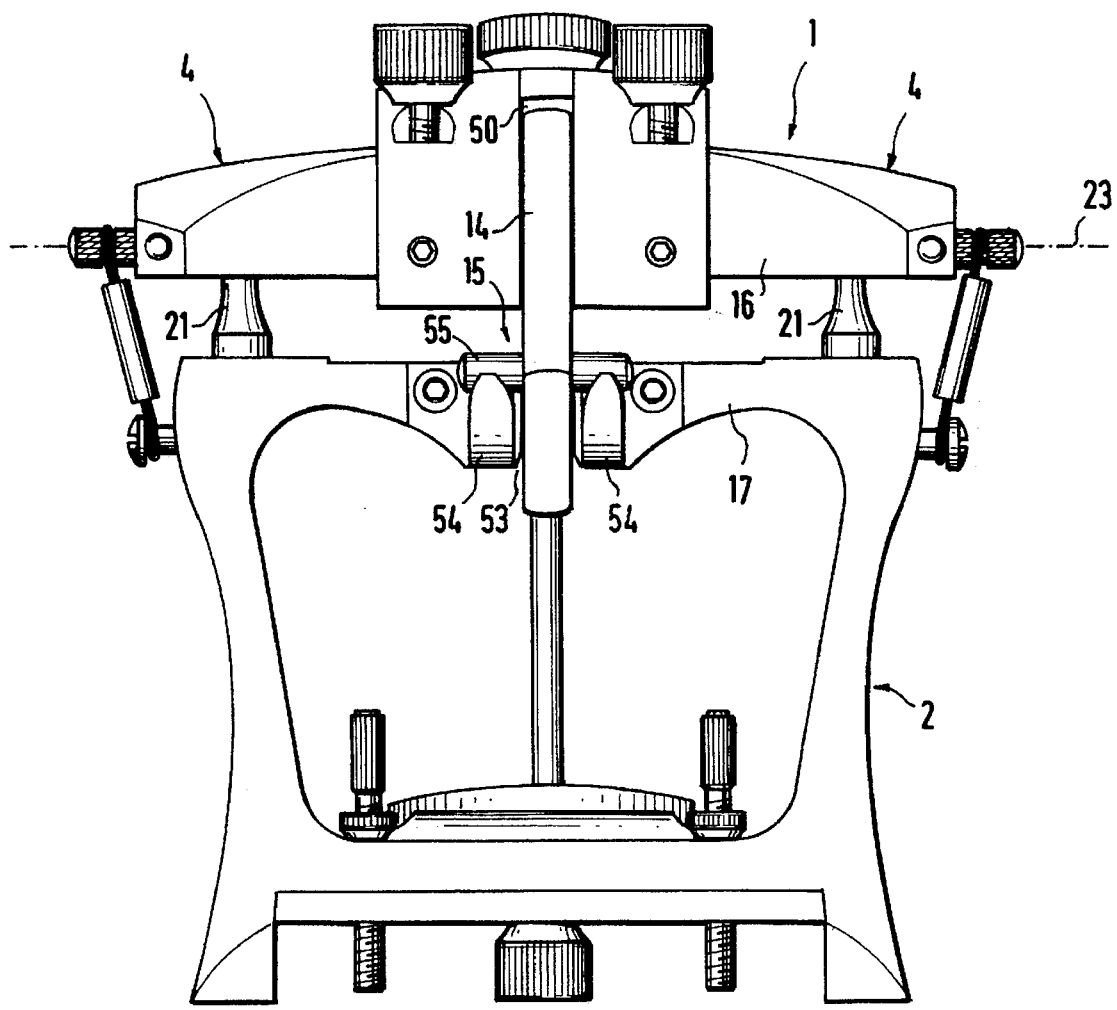
FIG. 3 is a rear view of the articulator.

As shown in FIGS. 1–3, the invention is embodied by an articulator comprising an upper part 1 pivoted to a lower part 2, adapted to bear an upper jaw and a lower jaw model respectively, on supporting plates 3 disposed on the underside. The upper and lower parts 1, 2 are connected by joints 4 so as to be pivotable and movable in a straight line (compare FIG. 10). A supporting pin 5 mounted in the upper part 1 extends downwards to a guide plate 6 mounted on the lower part 2 and the supporting pin 5 on guide plate 6 end rests in order to fix the bite height. A handhold 7 and handle 8 projecting upwards from the upper part 1 are used to impart pivoting and linear motions 22, 45, 46, 47 to the upper part 1 relative to the lower part 2 to simulate the movements of the jaw hinge, the movements being transmitted by the joints 4. Articulators of this kind are known per se, and the technical literature should be consulted for further details.

According to the invention, the upper and lower sides of the central portions 9, 10 of the upper 1 part and lower part 2 respectively, to which the supporting plates 3 are secured, are inclined at an angle 11 of 10°. As a result the central portions 9, 10 slope upwards, as seen in the dorsal direction 12 towards the joints 4.

As shown more particularly in FIGS. 2 and 3, the articulator according to the invention is provided with a centric locking device 13 disposed on the back of the articulator between the joints 4 and comprising two locking elements 14, 15 disposed on the upper and lower parts 1, 2. The locking elements are disposed approximately in the middle of the rear crossbars 16, 17 of the upper and lower part 1, 2.

The construction and operation of the articulator joint part 4 will now be explained with reference to FIGS. 4–9.

Figure 4:
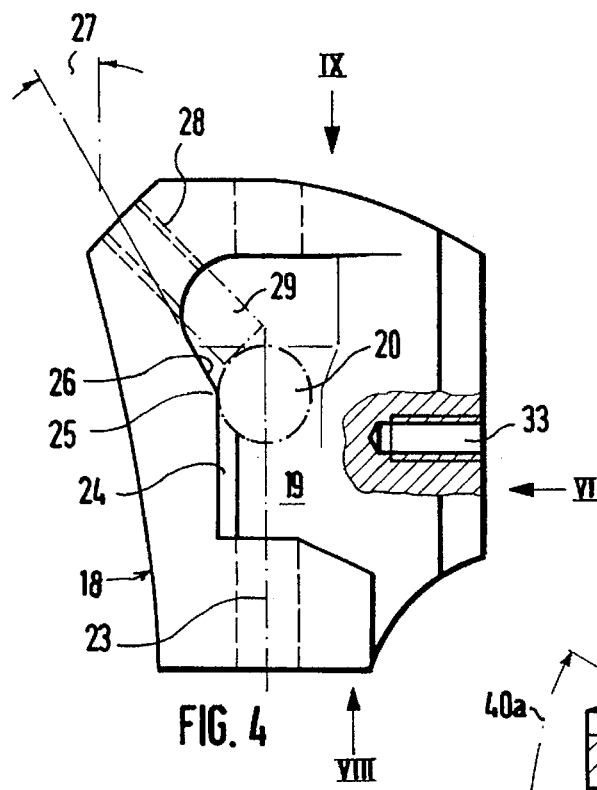
FIG. 4 is a horizontal plan view of the underside of the articulator joint box without the Bennett bevel.

The joint part substantially comprises a joint box 18 which, on its underside visible in FIG. 4, is formed with a cavity 19 for receiving the ball 20 of a joint. The joint box 18 constitutes the respective end of the crossbar 16 of the upper part 1, and the ball 20 is disposed at the tip of a shank 21 secured to the lower part 2 in the top lateral end region of the crossbar 17.

The ball 20 can roll on the wall bounding the cavity 19, which is concave and has a base radius of ¾ inches. The upper part 1 can therefore be made to pivot 22 relative to the lower part 2, substantially around an (imaginary) hinge axis 23 through the respective centers of the balls 20 of the two joints 4, so as to simulate movements of the lower jaw relative to the upper jaw. The hinge axis 23 extends perpendicular to FIG. 2 and in the plane of the drawing in FIGS. 3 and 4.

In FIG. 4, the ball 20 in the dorsal direction abuts a guide surface 24 forming a substantially straight track along which the ball 20 can slide. The guide surface or sliding track 24, as considered from medial to lateral, extends firstly in a portion parallel to the hinge axis 23 and then merges via a convex corner 25 into a sloping portion 26 which deviates from the direction of the hinge axis 23 by an angle 27 of about 30° in the retral/dorsal or retrusive direction. The sloping surface 26 consequently forms a guide surface or sliding track for simulating retrusion of the lower jaw relative to the upper jaw. The angle 27 of 30° results in a dynamic deviation of about 15° of the ball 20 relative to the hinge axis 23.

A through bore 28 opening into the cavity 19 of the joint box 18 has an inner thread in which a protrusion screw 29 can be rotated and thus moved in linear reciprocation. The bore 28 is aligned so that the protrusion screw 29 meshing therewith engages the ball 20 approximately in the region bounded by the sloping portion 26 and prevents it from retrusion or causes protrusion.

Figure 5:
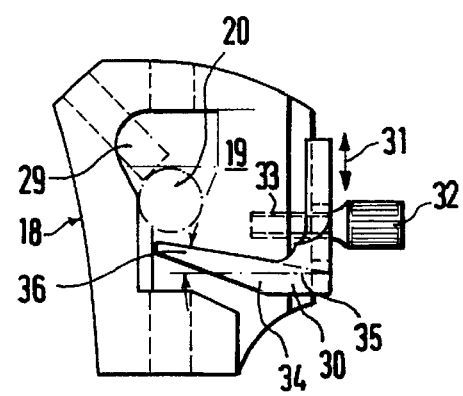
FIG. 5 is a corresponding plan view with the Bennett bevel acting on the joint box.

In FIG. 5, a Bennett bevel 30 extends into the cavity 19 of the joint box 18 and is mounted for reciprocation in the lateral/medial direction and can be locked in an internally threaded blind bore 33 by means of a milled-head screw 32. The part of the Bennett bevel which imparts a Bennett motion to the ball 20 is an arm 34 which projects into the cavity 19 in the joint box 18. The part of the arm facing the ball 20 forms a sliding track for the ball and is at an angle of about 10° to a line 35 extending parallel to the jaw median plane 44 or at right angles to the hinge axis 23.

Figure 6:
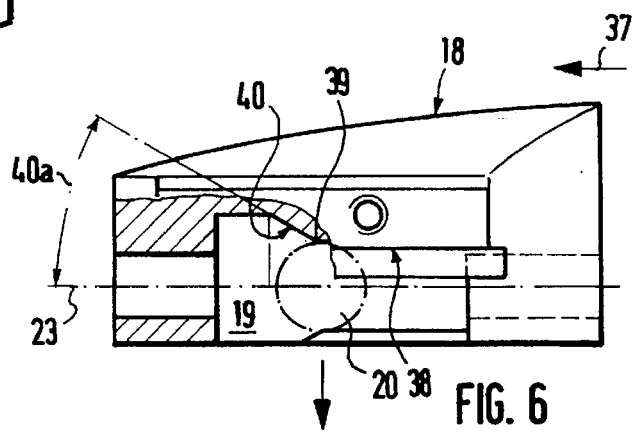
FIG. 6 is a front view in the direction VI in FIG. 4.
Figure 8:
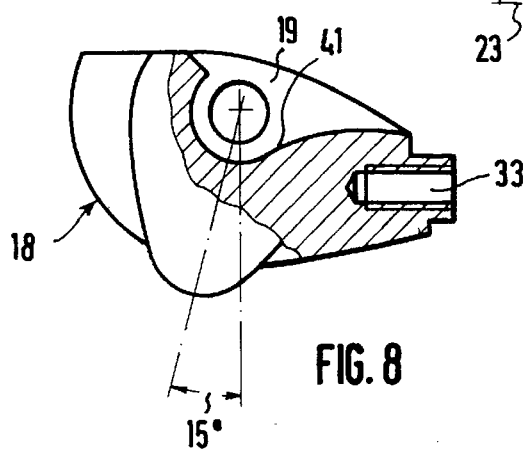
FIG. 8 is a side view in the direction VIII in FIG. 4.
Figure 7:
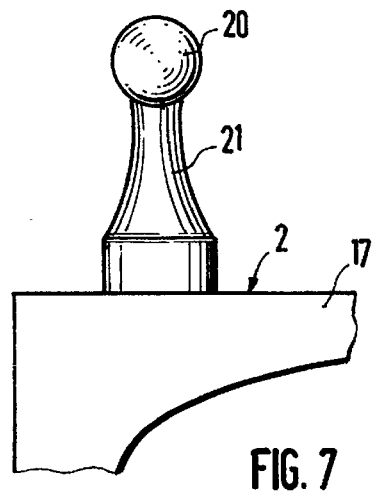
FIG. 7 is a side view of the ball of the joint for receiving in the joint box in FIGS. 4–6.
Figure 9:
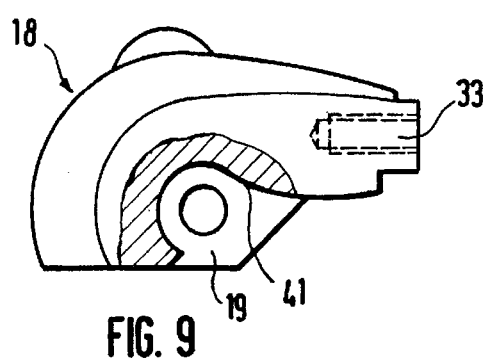
FIG. 9 is a view in the median direction IX in FIG. 4.

In FIG. 6, the ball 20 in the cranial direction also abuts the wall bounding the cavity 19 in the joint box 18. In the view in FIG. 6, the wall, as in FIG. 4, considered in the lateral direction 37, is divided into a first guide surface 38 parallel to the hinge axis 23 separated by a convex corner 39 from a following sloping portion 40 which diverges in the cranial or upward direction and is at an angle 40a of about 30° to the hinge axis 23. By this means, in addition to or alternatively to the 15° retrusion in FIG. 4, the ball 20 is given a motion reserve in the sense of a surtrusion of 15° relative to the hinge axis. If the motion reserve needs to include both the 15° retrusion (FIG. 4) and the 15° surtrusion (FIG. 6), the convex corners 25 (FIG. 4) and 39 (FIG. 6) can be regarded as points on a vertical line 41 which is drawn in FIGS. 8 and 9 and marks off the lateral guidance from the surtrusion and retrusion guidance of the ball 20.

Furthermore, with regard to the aforementioned Bennett bevel 30, the outside of the joint box 18 in FIG. 1 is constructed as an information carrier, i.e. comprises a 3-mm adjustment scale 42. The scale co-operates with a reference mark 43 in the form of a straight line on the second arm of the Bennett bevel, through which the milled-head screw 32 extends.

Figure 10:
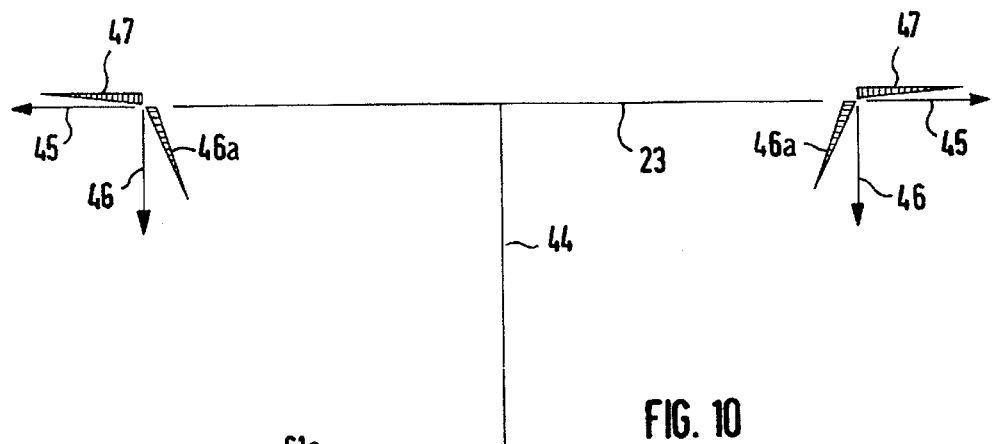
FIG. 10 is a diagrammatic horizontal plan showing movements of the lower jaw simulated by the articulator.

The horizontal plan in FIG. 10 additionally illustrates the operation of the retrusion and surtrusion guidance of the ball 20 on the lower jaw part 2. The horizontal line corresponds to the hinge axis 23 whereas the vertical line 44 is a plan view of the jaw median plane. In conventional articulators, the balls 20 can in any case move laterally, i.e. in the laterotrusion direction 45. For additional clarity, the "immediate side shift" 46a is also shown by a shaded triangle extending in the region bounded by the hinge axis 23 and the median plane 44. The protrusion parallel to the medial plane 44 is marked 46. The sloping portion 26 in FIG. 4 is for retrusion 47 of the ball 20, as illustrated by the shaded triangle marked 47, which extends outside the region bounded by the hinge axis line 23 and the median line 44. The diagram in FIG. 10 can also be interpreted as a frontal plane, in which case the last-mentioned shaded triangle 47 will represent the surtrusion, brought about by the sloping portion 40 in FIG. 6, which serves as a sliding and guiding track for the ball 20.

Figure 11:
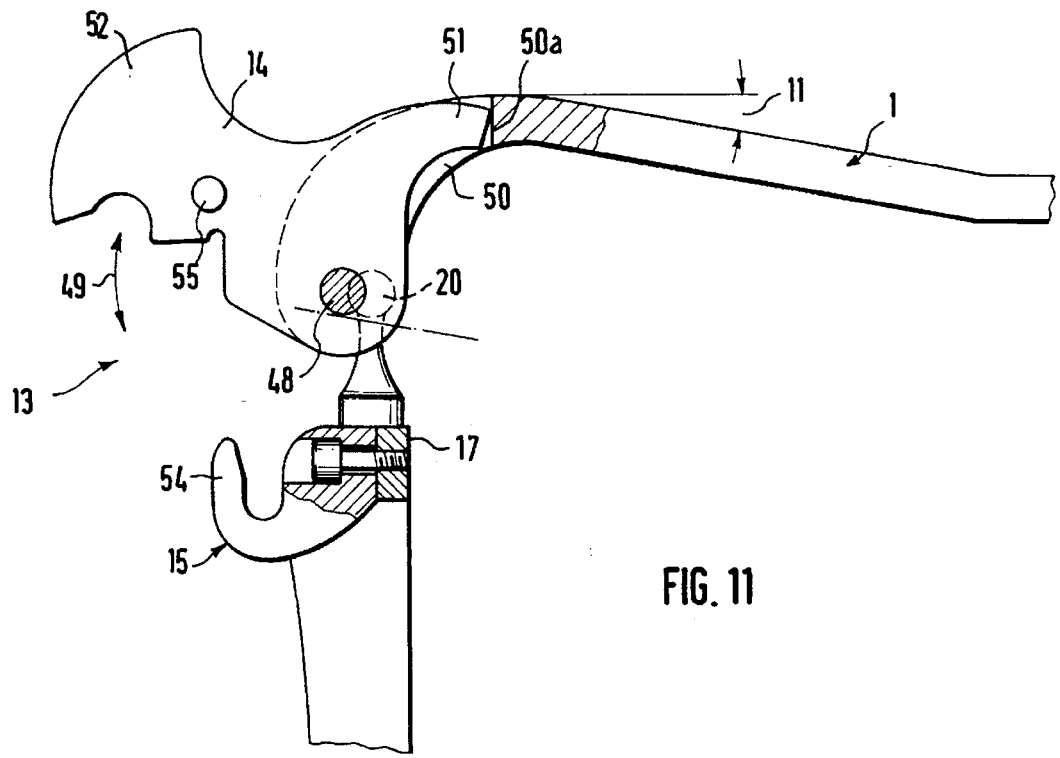
FIG. 11 is a larger-scale portion of a side view of the centric locking means in the opened position.
Figure 12:
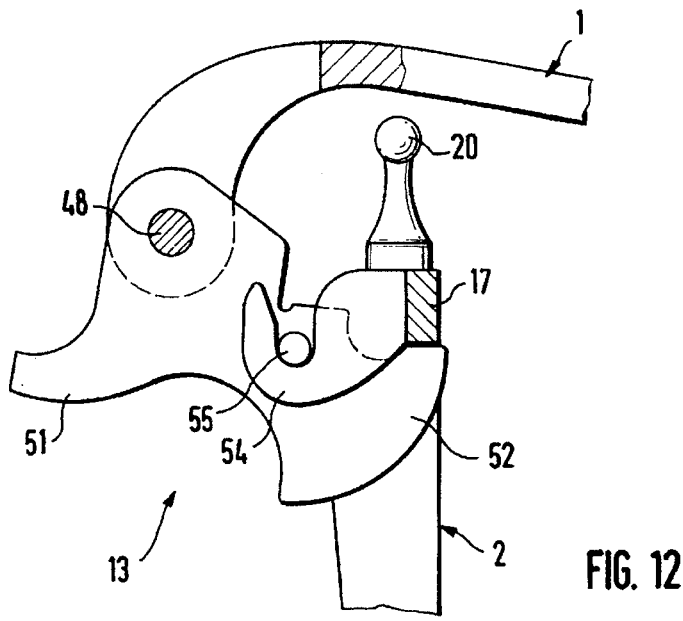
FIG. 12 is a corresponding view of the centric locking means in the closed position.

The centric locking means 13 will be explained in detail with reference to FIGS. 3, 11 and 12. The first locking element 14 is connected via a pivot 48 to the upper part 1 of the articulator. It is in the form of a narrow insertion means which, owing to its flat shape, can easily be pivoted 49 either to the second locking element 15 or into an abutment gap 50, disposed at the rear and centrally in the crossbar of the upper part 1. In FIG. 11, the lug 51 of the first locking element or insertion means 14 has struck the end 52 of the gap 50. In the position in FIG. 11, the ball 20 can move laterally relatively to the joint box 18. To prevent such movements, i.e. for centric locking of the upper and lower parts 1, 2 relative to one another, the insertion means is pivoted 49 downwards into the position in FIG. 3. In this position, the handling attachment 52 of the insertion means 44 is pushed into a locking gap 53 bounded by two upwardly open catch hooks 54. The hooks together form the second locking element 15 or its locking gap 53 and secure the attachment 52 or upper locking element 14 to the upper part 1. On each side, the upper part has a laterally extending suspension projection 55 which, in the centrically locked position in FIG. 3, abuts the crossbar 17 of the lower part 2 but has not yet been fully pushed or received in the catch fork formed by the two spaced-apart hooks 54. This is possible only when the ball 20 has been disengaged from the joint box 18 and is free as per FIG. 12. In that case the top part 1 and joint 48 is moved relative to the crossbar 17 backwards (dorsally) and downwards (caudally) so that the projections 55 rest in the two hooks 54 forming the fork. The upper part can then be pivoted through about 180° around the joint 48, so that the e.g. rubber-like handle part 8 of the handhold. 7 rests on a table surface or the like. This position (not shown) is suitable for attaching upper or lower jaw models 100 to the plates 3 (see FIG. 2) or removing them therefrom.

Figure 13:
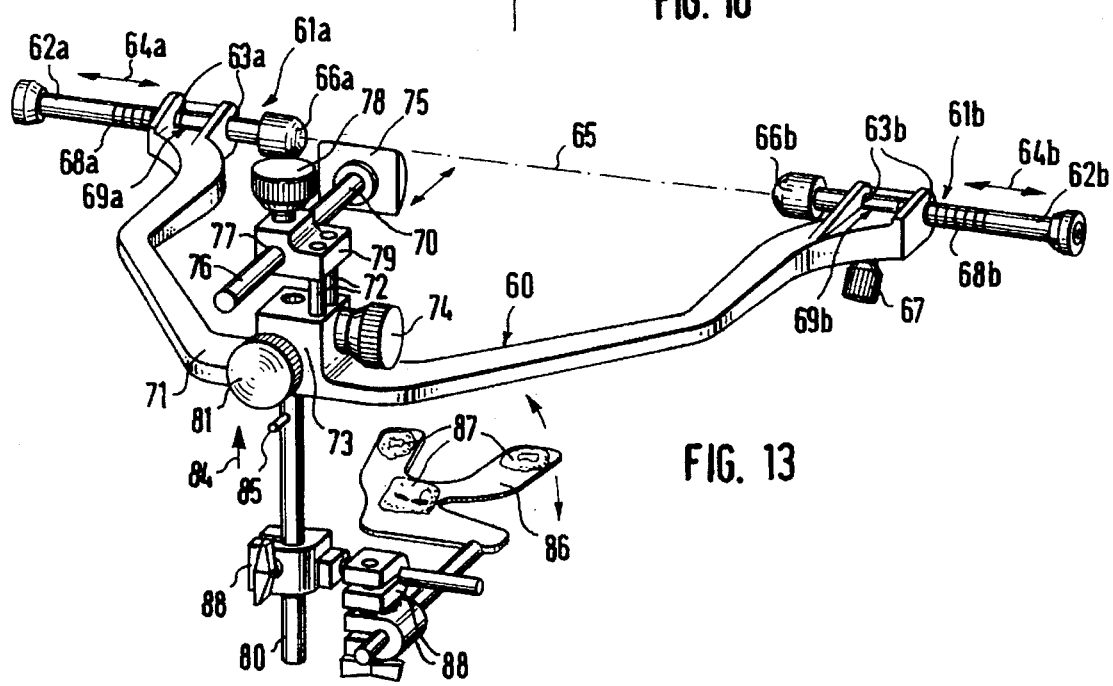
FIG. 13 is a perspective view of the face bow according to the invention with a vertical guide column and a bite fork mounted thereon.

In FIG. 13, a face bow comprises a curved transfer member 60 for receiving and transferring a model jaw in the correct three-dimensional orientation relative to the skull in the previously-explained articulator. Measuring pins 62a, 62b extend through the end regions 61a, 61b respectively and are guided for movement in bores 63a, 63b. The guide bores 63a, 63b are symmetrically aligned with one another so that the two pins 62a, 62b or their respective sliding movements 64a, 64b are in a common alignment 65. In order to locate the reference points for the jaw hinge axis on the human skull, the padded heads 66a, 66b (e.g. of plastics) of the pins 62a, 62b are inserted part of the way into the patient's auditory canals and secured in position by milled-head screws 67. Care is taken to keep the end regions 61a, 61b of the transfer member 60 at the same distance from the sides of the patient's face or his auditory canals. To this end the pins 62a, 62b each carry colored coding rings 68a, 68b. In order to set equal distances to the patient's auditory canals, the code rings 68a, 68b are moved past the associated reference marks 69a, 69b or fixed relative to them. By means of the color coding, the adjustment can be made so that the padded heads 66a, 66b project from the ends 61a, 61b of the transfer member for the same distance towards the auditory canals, so as to obtain symmetry relative to the jaw median plane.

The face bow in FIG. 13 is also attached by using the patient's glabella, by means of a supporting projection 70. The projection 70 is guided in a straight line on the top surface of the transfer member 60, in its central portion 71 and at right angles to the plane of the transfer member. The guide system comprises two parallel rods 72 which can be inserted into a central raised portion 73 and locked by a milled-head screw 74. Another guide for the glabella supporting projection 70 is provided parallel to and at a distance from the plane spanned by the transfer member 60. The second guide is in the form of a shank 76 bearing a glabella pad 75 and movable in reciprocation in a bore 77 and adapted to be locked therein by a milled head screw 78. The distance from the guide bore 77 to the transfer member 60 can be adjusted by moving the two rods 72 and securing them by the screw 74. The two rods 72 are for stabilizing the alignment of the guide bores 77 relative to the glabella. They therefore bear an attachment 79 through which the guide bore 77 extends.

Figure 14:
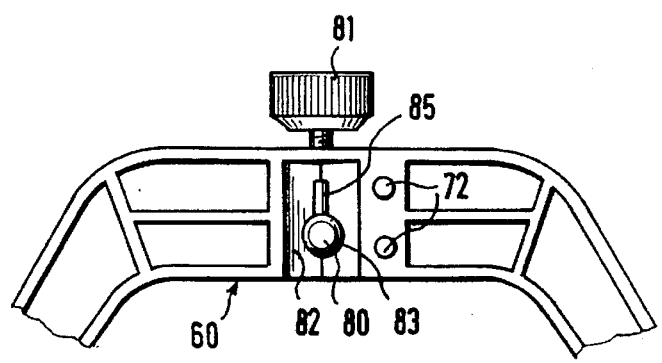
FIG. 14 is a plan view of the underside of the central portion of the face bow with the centring recess and the adjusting projection disposed therein.

Below the central raised portion 73 of the transfer member 60, a guide column 80 is movable and can be received and locked by a milled head screw 81. As shown by the plan view of the underside of the transfer member 60 in FIG. 14, a guide bore 83 extends transversely through a centring groove 82 having an approximately V-shaped cross-section.

The guide bore 83 is aligned so that the guide column can move at right angles to the plane spanned by the transfer member 60. The abutment element is an adjusting spike 85 which is attached to the guide column 80 and projects vertically therefrom and, if necessary, rests in the centring groove 82 when the guide column 80 is inserted into the guide bore 83. The spike 85 is also used for securing the guide column 80 in a rotary position in the transfer member 60. Next, a bite fork 86 (compare FIG. 13) in the patient's mouth (not shown) and bearing a wax recording means 87 with impressions of the patient, is secured to the guide column 80 by clamping elements 88. During the securing process, the measuring pins 62a, 62b of the transfer member 60 are positioned in accordance with the jaw hinge axis of the patient.

Figure 15:
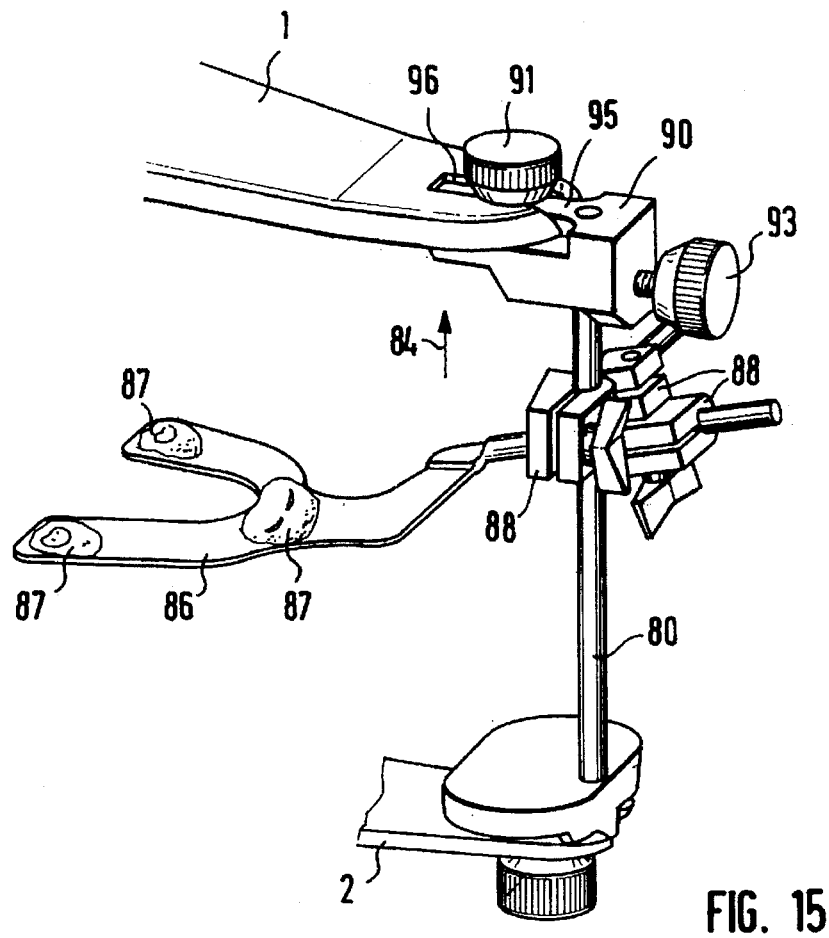
FIG. 15 is a perspective view of the upper jaw articulator part and the adapter secured thereto.
Figure 16:
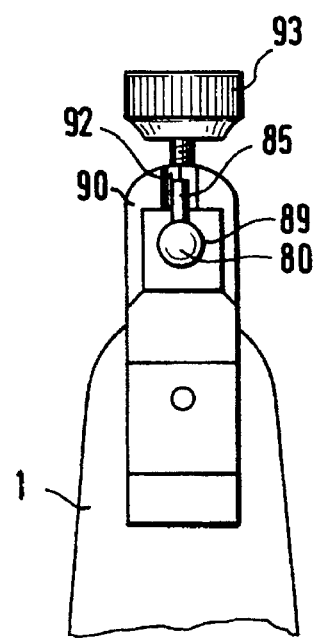
FIG. 16 is a plan view of the underside of the adapter, showing the centring recess and the adjusting projection therein.

Next, as in FIG. 15, the guide column 80 is released from the transfer member 60 and partly inserted into an additional guide bore 89 (compare FIG. 16) through an adapter part 90 secured to the upper part 1 by a milled-head screw 91. When the guide column 80 is inserted 84 further into the adapter guide bore 89, the spike 85 comes against the top of the V-section centring groove 92 on the underside of the adapter part 90, as shown in FIG. 16.

This position can be fixed by a milled-head screw 93 operating in the guide bore 89. The guide column 80 is thereby rotated into the same position as its previous position in the transfer member 60 of the face bow in FIG. 14.

The bite fork 86 has been fixed in the correct three-dimensional position relative to the skull by means of the clamping elements 88. If no change has been made in this position, the bite fork 86 in the articulator has a three-dimensional orientation to the hinge axis 23 of the two balls 20 (compare FIGS. 1 and 10) which corresponds very closely to the characteristics of the patient, as measured by the pins 62a, 62b, the glabella supporting projection 70 and the bite fork 86 and wax recording means 87.

The adapter 90 is a part compatible with the conventional articulator upper part 1, and can be replaced by the holding part 94 for adjusting the height of the supporting pin 5 (compare FIG. 1). To this end the adapter part 90 has a raised elongate rear web 95 which can be inserted into the front slot 96 in the upper part 1 of the articulator (compare FIG. 15 and FIG. 1).

I claim:

1. A dental apparatus including a face bow for receiving and transferring a model jaw in the correct spatial orientation relative to a patient's skull and jaw hinge axis to a jaw articulator, the face bow comprising a curved transfer member for surrounding a patient's face and a guide column releasably secured to the transfer member for carrying an adjustable bite fork, the transfer member having an elongate centering groove and the guide column having an adjusting projection, which is perpendicular to the guide column for engagement in the centering groove, the dental apparatus further including an adapter connectable to the bite fork guide column, attachable to a pivoted upper part of the jaw articulator, and having a corresponding elongate centering groove for receiving the adjusting projection and rotationally aligning the guide column when the guide column is removed from the transfer member and mounted to the adapter.

2. An apparatus in accordance with claim 1 wherein the adapter has a bore for receiving the guide column, the bore being positioned with the centering groove of the adapter radially disposed near an opening edge of the bore.

3. A dental apparatus in accordance with claim 1 wherein the face bow has end regions comprising scanners for attaching the transfer member at the jaw hinge axis, the scanners being movable along the hinge axis and lockable.

4. An apparatus in accordance with claim 3 wherein the scanners bear code markings which are symmetrical relative to a median plane of the jaw extending transversely to the hinge axis and adapted for movement past stationary adjustment markings on the transfer member.

5. An apparatus in accordance with claim 4 wherein the scanners are pins which extend through opposite ends of the transfer member in the direction of the hinge axis and the code markings are color coded rings surrounding the pins.

6. An apparatus in accordance with claim 3 wherein the face bow further comprises a supporting projection disposed in a central portion of the transfer member for abutting the glabella.

7. (Amended) An apparatus in accordance with claim 6 wherein the supporting projection is movably adjustable in directions towards a patient's glabella and transversely to a plane spanned by the transfer member and lockable in a selected position of adjustment.

8. An apparatus in accordance with claim 1 wherein the adapter is releasably attachable to the upper part of the articulator.

9. A dental apparatus in accordance with claim 1 wherein the adjusting projection is a perpendicularly projecting spike.

10. A dental apparatus in accordance with claim 1 wherein the centering groove is substantially at right angles to the hinge axis.

11. A dental apparatus including a face bow for receiving and transferring a model jaw in the correct spatial orientation relative to a patient's skull and jaw hinge axis to a jaw articulator, the face bow comprising a curved transfer member for surrounding a patient's face and a guide column releasably secured to the transfer member for carrying an adjustable bite fork, the transfer member having an elongate, V-section centering groove and an adjusting projection, which is perpendicular to the guide column for engagement in the centering groove.

12. A dental apparatus in accordance with claim 11 wherein the centering groove is substantially at right angles to the hinge axis.

13. A dental apparatus in accordance with claim 12 wherein the centering recess extends substantially in a central plane of the transfer member. angles to the hinge axis.

14. A dental apparatus in accordance with claim 11 wherein the adjusting projection is a perpendicularly projecting spike.

15. A dental apparatus in accordance with claim 11 wherein the face bow has end regions comprising scanners for attaching the transfer member at the jaw hinge axis, the scanners being movable along the hinge axis and lockable.

* * * * *